(12) United States Patent
Erm et al.

(10) Patent No.: US 10,030,222 B2
(45) Date of Patent: Jul. 24, 2018

(54) BIOREACTOR SYSTEM AND METHOD FOR CLONING THE PHYSIOLOGICAL STATE OF MICROORGANISMS

(71) Applicants: TALLINN UNIVERSITY OF TECHNOLOGY, Tallinn (EE); TOIDU- JA FERMENTATSIOONITEHNOLOOGIA ARENDUSKESKUS AS, Tallinn (EE)

(72) Inventors: Sten Erm, Tallinn (EE); Raivo Vilu, Tallinn (EE); Kaarel Adamberg, Harjumaa (EE)

(73) Assignees: TALLINN UNIVERSITY OF TECHNOLOGY, Tallinn (EE); TOIDU—JA FERMENTATSIOONITEHNOLOOGIA ARENDUSKESKUS, Tallinn (EE)

( * ) Notice: Subject to any disclaimer, the term of this patent is extended or adjusted under 35 U.S.C. 154(b) by 558 days.

(21) Appl. No.: 14/401,541

(22) PCT Filed: May 15, 2013

(86) PCT No.: PCT/EE2013/000005
§ 371 (c)(1),
(2) Date: Nov. 17, 2014

(87) PCT Pub. No.: WO2013/170863
PCT Pub. Date: Nov. 21, 2013

(65) Prior Publication Data
US 2015/0140544 A1    May 21, 2015

(30) Foreign Application Priority Data
May 16, 2012  (EE) .................................. 201200008

(51) Int. Cl.
*C12M 1/00* (2006.01)
*C12M 1/26* (2006.01)
(Continued)

(52) U.S. Cl.
CPC ............ *C12M 41/14* (2013.01); *C12M 23/40* (2013.01); *C12M 23/44* (2013.01); *C12M 23/58* (2013.01);
(Continued)

(58) Field of Classification Search
CPC ...... C12M 41/14; C12M 23/40; C12M 23/44; C12M 23/58; C12M 27/02; C12M 33/14;
(Continued)

(56) References Cited

U.S. PATENT DOCUMENTS 4,976,377 A * 12/1990 Higuchi .................... G01F 1/76
                                                   137/487.5
2010/0041124 A1   2/2010 Chang et al.
2011/0236937 A1   9/2011 Smith et al.

FOREIGN PATENT DOCUMENTS

BG        50222 A1   5/1996
DE    19547656 A1   6/1997
(Continued)

OTHER PUBLICATIONS

International Search Report for PCT/EE2013/000005, dated Sep. 24, 2013.
(Continued)

*Primary Examiner* — William H Beisner
*Assistant Examiner* — Danielle B Henkel
(74) *Attorney, Agent, or Firm* — Berggren LLP

(57) ABSTRACT

Bioreactor system and method for cloning the physiological state of microorganisms comprises in preferred embodiment of a mother-reactor and one or more daughter-reactors with sensors, stirrers, fluid and gas flow channels, scales, pumps,
(Continued)

controllers, computer, software, valves and accessory devices. The bioreactors are inter-connected with culture transfer hose. To achieve the method, the mother-reactor is filled with necessary volume, inoculated, stabilised in continuous cultivation, the microbial culture's volume is increased in variable volume cultivation while maintaining constant physiology, microbial culture is transferred from the mother-reactor into the daughter-reactors while maintaining constant physiology, experiment in the daughter reactor follows. After the experiment daughter-reactors are sterilized and rinsed. During the experiment culture volume in the mother-reactor is increased anew, after the experiment in the daughter-reactors is finished another culture transfer follows and next experiment is conducted. This sequence—variable volume cultivation, culture transfer, experiment—is repeated until necessary data has been acquired.

16 Claims, 9 Drawing Sheets

(51) Int. Cl.
C12M 1/34 (2006.01)
C12M 3/00 (2006.01)
C12M 1/06 (2006.01)
C12M 1/02 (2006.01)
C12M 1/36 (2006.01)

(52) U.S. Cl.
CPC ............ C12M 27/02 (2013.01); C12M 33/14 (2013.01); C12M 41/12 (2013.01); C12M 41/24 (2013.01); C12M 41/34 (2013.01); C12M 41/40 (2013.01); C12M 41/44 (2013.01); C12M 41/48 (2013.01); C12M 43/00 (2013.01); C12M 45/20 (2013.01)

(58) Field of Classification Search
CPC ...... C12M 41/12; C12M 41/24; C12M 41/32; C12M 41/34; C12M 41/40; C12M 41/44; C12M 41/48; C12M 43/00; C12M 45/20
See application file for complete search history.

(56) References Cited

FOREIGN PATENT DOCUMENTS

| | | |
|---|---|---|
| GB | 1270006 A | 4/1972 |
| JP | 08229534 A | 10/1996 |
| WO | 03020919 A2 | 3/2003 |
| WO | 2005042694 A2 | 5/2005 |
| WO | 2008070561 A1 | 6/2008 |

OTHER PUBLICATIONS

J. Fricke, et al. "A multi-bioreactor system for optimal production of malaria vaccines with Pichia pastoris," Biotechnology Journal 2011, vol. 6(4), pp. 437-451.

Hortsch, et al. "A Two-stage CSTR Cascade for Studying the Effect of Inhibitory and Toxic Substances in Bioprocesses," Engineering in Life Sciences 2008, vol. 8(6), pp. 650-657.

Fu, et al. "Continuous, high-level production and excertion of a plasmid-encoded protein by *Escherichia-coli* in a two stage chemostat," Biotechnology and Bioengineering 1993, vol. 41(10), pp. 937-946.

Delvigne, et al. "Bioreactor mixing efficiency modulates the activity of a prpoS::GFP reporter gene in *E. coli*," Microbial Cell Factories 2009, vol. 8.

Barrick, et al. "Genome evolution and adaptatiopn in a long-term experiment with *Escherichia coli*," Nature 2009, 461, pp. 1243-1247.

* cited by examiner

BIOREACTOR SYSTEM AND METHOD FOR CLONING THE PHYSIOLOGICAL STATE OF MICROORGANISMS

PRIORITY

This application is a national entry of PCT/EE2013/000005 filed on May 15 2013, which claims priority of Estonian national patent application number P20120008 filed on May 16, 2012, both of which are fully incorporated herein by reference.

TECHNICAL FIELD

The present invention belongs to the solutions for cultivating microorganisms for research and production purposes, more specifically to the field of reactor systems combined of several individual bioreactors. Cultivation processes are comprised of batch, fed batch and continuous cultivations.

BACKGROUND OF THE INVENTION

In studying physiology of microorganisms it is important to vary only the parameter the effects of which are being studied. For example, if the effect of temperature change is being studied then pH and other parameters should be fixed and remain constant. In addition, microorganisms under the study should not be affected by stress caused due to the lack or excess of the substrate. If the transfer from one reactor to another is slow, an uncontrolled growth of microorganisms will take place in transfer hoses—the residual substrate will be consumed, the starvation will follow which in turn will lead to activation of various stress responses (microbial culture is no longer in a state of stable physiology). If in the beginning of the experiment microbial culture is in unstable physiological state there is always a possibility that the result is not due to the variable parameter. Thus, the constancy of physiological state after the culture transfer is an important criterion in all bioreactors within the system if the wish is to carry out experiments or production processes in identical starting conditions. Similarly, the physiological state should remain constant in the phase of increasing the volume to obtain unambiguous response to changes in environmental parameters throughout later cultivation. If in case of continuous cultivation a microbial culture is in unstable physiological state at the starting point of the experiment a stabilisation phase, which usually is five residence times, must precede. Thus, if the physiological state is altered accidentally during cultivation process (increasing of the volume or transfer of microbial cultures) duration of the experiment will increase by a stabilisation phase.

Several cultivation technologies are known using different bioreactor systems. Continuous, batch and fed batch cultivations have been used the most in interconnected bioreactors.

A system consisting of one 5 L mother reactor and of six 1 L daughter reactor(s) was described in the article "A multi-bioreactor system for optimal production of malaria vaccines with *Pichia pastoris*" J. Fricke, K. Pohlmann, F. Tatge, R. Lang, B. Faber, R. Luttmann, Biotechnology Journal 2011, vol 6 (4), pp 437-451. An increase of the volume of biomass in fed batch cultivation takes place in the mother reactor, after that microbial culture is transferred to the daughter reactor. The disadvantage of this solution is alteration of other parameters besides volume in the mother reactor (micro-organisms are processed with methanol to induce synthesis of recombinant protein). Also, during increase of the volume the temperature in mother reactor is lowered from 30° C. to 20° C. resulting in unstable physiology of microorganisms. The transfer is followed by regrowing of the microbial population volume in the mother reactor, but due to the effects of previous methanol and temperature alterations new microbial culture has potentially different physiological state compared to the original culture. In addition, this solution does not enable the preservation of the same physiological state in mother- and daughter-reactors after the transfer. One solution described in the article prescribes a 30° C. temperature in mother reactor and 20° C. in daughter-reactor, which consequently leads to different physiological state. Stabilisation to the new conditions can be observed in the results of the study, as the concentration of methanol fluctuated after the transfer of culture. The second solution prescribed an identical initial temperature in mother- and daughter reactor(s), but in daughter reactor the microbial culture was diluted twofold with a fresh feed. Although the transfer was conducted in a periodical manner, different environmental conditions were applied in some daughter-reactors (temperature, pH, concentration of methanol). Thus, environmental parameters are abruptly changed during the transfer, which results in stress response of microorganisms. Detailed description of the technical solution is not presented in this article, so it can be assumed that the rapid transfer rate of microbial culture was not considered a critical parameter. However, it is important to keep in mind that during the fed batch cultivation, where concentration of biomass is high and consequently so is the oxygen consumption rate, an anaerobic environment is very likely to occur in case of a slow transfer which in turn results in changes in physiology. Possible problems in maintaining aerobic environment can be seen from a fluctuating $Q_{O2}$ line in FIG. 7 of the article.

In the article "A Two-stage CSTR Cascade for Studying the Effect of Inhibitory and Toxic Substances in Bioprocesses", R. Hortsch, C. Loser, T. Bley, "Engineering in Life Sciences", 2008, vol 8 (6), pp 650-657 a cultivation system with continuous transfer between reactors is described. This solution does not allow a periodical transfer of microbial culture. Since the flow of biomass in daughter reactor is twice as high as in the mother reactor due to additional substrate necessary for growth of the biomass, cultivation method and consequently the physiological state of microorganisms is not the same in mother and daughter reactor(s) after transfer. A slow peristaltic pump was used for the biomass transfer in this solution, which is not fast enough to transfer biomass with unchanging physiology.

The article "Continuous, high-level production and excertion of a plasmid-encoded protein by *Escherichia-coli* in a two-stage chemostat", J. Fu, D. B. Wilson, M. L. Shuler, "Biotechnology and Bioengineering", 1993, vol 41 (10), pp 937-946 describes a system with continuous transfer of microbial culture from mother- to daughter reactor, with different dilution rates in two reactors and a continuous induction of protein synthesis with IPTG (Isopropyl β-D-1-thiogalactopyranoside) in daughter reactor. Due to differences in environmental conditions in mother- and daughter reactor(s) it is not possible to perform a transfer of microbial culture without changing its physiological state, resulting in different conditions in mother- and daughter-reactors from the beginning of the experiment.

Article "Bioreactor mixing efficiency modulates the activity of a prpoS::GFP reporter gene in *E. coli*", F. Delvigne, M. Boxus, S. Ingels, P. Thonart, "Microbial Cell Factories", 2009, vol 8 describes a system with a fed batch cultivation and continuous transfer of biomass from stirred tank reactor to plug flow reactor to imitate heterogeneity of the content of industrial bioreactor (different gradients of nutrients or other environmental parameters in different parts of bioreactor). Concentrated glucose solution was added to microbial culture in plug flow reactor and the culture was not aerated. In this case, a transfer of microbial culture from one reactor to another is continuous, meaning that in daughter reactor the experiment cannot be started with a culture stabilised in the mother reactor. Different cultivating methods are applied in different reactors (chemostat in stirred tank reactor and batch cultivation in plug flow reactor). From the plug flow reactor biomass is directed back to the stirred tank reactor, thus altering a physiological state of the fed batch culture in mother reactor.

In the article "Genome evolution and adaptation in a long-term experiment with *Escherichia coli*", J. E. Barrick, D. S. Yu, S. H. H. T. K. Oh, D. Schneider, R. E. Lenski, J. F. Kim, "Nature", 2009, 461, pp 1243-1247 the most widely used reactor-to-reactor transfer solution is described, where batch cultivation is repeated in order to achieve a greater number of microorganisms generations. In the phase of exponential growth bacteria are planted into a sterile culture medium and nurtured after what transfer and the rest of procedure are repeated. During the transfer a dilution of microbial culture takes place, resulting in stress response of microorganisms. In addition, stirring is suspended in bioreactor during the transfer, which leads to decline of oxygen solubility and along with that to changes in microbial physiology.

Bioreactor systems where transfer of microbial cultures is applied occur in several patent documents. The biggest disadvantage of these solutions so far is that they do not allow the transfer of microbial culture in strictly controlled environment thus in different reactors the physiological state is different. Solutions described in the following patent documents are good examples for that.

German patent application DE19547656A1 describes sequential reactors to detect toxic substances from wastewater. The transfer of microbial culture between reactors is described, but preservation of constant physiological state is missing. The transfer is continuous, physiological state varies in different reactors which means that the experiment cannot be started in daughter reactor with microbial culture stabilised in mother reactor. During cultivation the volume in mother reactor remains constant. This solution does not allow the optimisation of the process of microbial transfer. The UK patent GB1270006 describes the series of reactors where microbial culture is kept in continuous logarithmic growth phase, meaning that due to the effect of diluting with media, concentrations are altered during the transfer and physiological state is not constant. Japanese patent application JP8229534A describes the transfer of culture from one reactor to another focusing not on the fixed physiological state at the beginning of the experiment but rather on obtaining different summary conversion rates in different reactors. Patent application WO2005042694A2 describes a system of transfer of microbial culture between bioreactors where physiological state of microorganisms is altered during the process. Different cultivation methods are applied in different reactors which makes starting the experiment with a stabilised culture impossible. Solution described in Bulgarian patent BG50222A does not allow the transfer of microbial culture in controlled conditions nor preservation of the physiological state. The USA patent application US2010041124A1 describes a multi-stage bioreactor system where microorganisms are transferred between reactors, but since medium is inserted only in the first reactor this solution does not allow to start experiments with the same physiological state in different reactors. Biomass concentration in different reactors is not identical.

Solutions known to date do not allow the transfer of microbial culture between different reactors in controlled conditions nor using the same cultivation method which makes preservation of the physiological state, environmental conditions and biomass parameters during the transfer impossible. Due to different cultivation methods in different reactors the solutions known to date render it impossible to start cultivations after the transfer with a stabilised culture in different reactors. Due to different environmental conditions in different reactors it is impossible to transfer microbial culture without interfering its physiological state and the experiment cannot be started in daughter reactor with conditions identical to those of the stabilised culture in mother reactor.

SUMMARY OF THE INVENTION

The purpose of the current invention is to provide a bioreactor system and a method for cloning the physiological state of microorganisms and the further research, free of the afore-mentioned disadvantages, for production of biomass or metabolites (like ethanol, recombinant protein) or other biological compounds (like RNA, protein, polysaccharide). Hereinafter the experiment or production process taking place after the transfer is referred to as "the experiment".

Unlike previously known solutions, the physiological state of microorganisms in the current invention is maintained constant during variable volume cultivation, during as well as after the transfer of microbial culture. This means that measurable parameters of biomass during variable volume cultivation and in different reactors after the transfer of microbial culture (from 0.01 seconds up to 100 hours) do not change by more than 20% compared to initial parameters in mother reactor prior to the increase of volume. The number of parameters measured during the process is not limited. In alternative embodiment the physiological state during the variable volume cultivation is changed by the user deliberately; however the physiological state must be defined by the cultivation algorithm at all times and must be applicable in a reproducible manner.

Unlike solutions known so far the current bioreactor system and method for cloning the physiological state of microorganisms allows, without disturbing the physiological state, to:

perform variable volume cultivation in mother reactor at fixed environmental conditions (dispersion of environmental parameters is allowed but must not result in alteration of the physiological state of the cells compared to the initial physiological state by more than 20%);

perform variable volume cultivation in the mother reactor with changing physiological state, however the physiological state must be defined by the cultivation algorithm at all times and must be applicable in a reproducible manner.

prior to the transfer set the environmental parameters in daughter reactor(s) to match those in the mother reactor (dispersion of environmental parameters is allowed but must not result in alteration of the physiological state of the cells compared to the initial physiological state by more than 20%), daughter reactor(s) do not contain fluids prior to the transfer (0.1-3600 seconds);

apply the same environmental parameters in mother and daughter reactor at the moment of transfer (dispersion of environmental parameters is allowed but must not result in alteration of the physiological state of the cells compared to the initial physiological state by more than 20%);

transfer into emptied daughter reactor(s) with preset environmental parameters;

apply identical environmental parameters in the mother reactor and daughter reactor(s) after the transfer of microbial culture (dispersion of environmental parameters is allowed but must not result in alteration of the physiological state of the cells compared to the initial physiological state by more than 20%);

apply cultivation parameters corresponding to the biomass amount at the moment of transfer and after that;

perform a periodical transfer of microbial culture;

perform a fast enough transfer of microbial culture (volume transfer within 0.01-3600 seconds) (critical transfer time is determined by the biomass parameters such as density, substrate concentration and consumption rate, minimal control interval of cultivation process);

apply the same cultivation method in different reactors after the transfer;

apply different cultivation methods in different reactors after the transfer;

stabilise microbial culture in mother reactor in case of continuous cultivation one time only which reduces the time required for stabilisation as well as the amount of substrate during the following transfers and experiments;

conduct variable volume cultivation during the stabilisation phase, resulting in optimized experiment time;

transfer biomass from mother reactor to daughter reactor preserving the initial fixed physiological state in all reactors in the system (dispersion of the physiological state no more than 20%);

start the experiment with identical initial environmental conditions in all reactors of the system (dispersion of environmental parameters is allowed but must not result in alteration of the physiological state of the cells compared to the initial physiological state by more than 20%);

start the experiment with biomass in identical physiological state in all reactors of the system (dispersion of physiological state of biomass not by more than 20%);

vary the reactor in which variable volume cultivation takes place (mother reactor in one experiment can be used as daughter reactor in the following experiment in the next iteration);

vary the reactor into which transfer of microbial culture takes place (daughter reactor in one experiment can be used as mother reactor in the following experiment in the next iteration);

Bioreactor system used to achieve these goals consists of at least one mother reactor and at least one daughter reactor, equipped with sensors and controllers and connected to a control device equipped with proper control software. Unlike other inventions known to date, the current invention keeps the studied microorganisms continuously under defined and controlled physiological state that is achieved by using necessary cultivation methods. In preferred solution following the transfer and before the experiment in daughter reactor(s), cultivation method and environmental conditions are equal in all reactors, in alternative realisation of the experiment different cultivation methods are applied in different reactors, but the physiological state must remain unaltered (for example a continuous cultivation in the mother reactor and fed batch cultivation in daughter reactor(s)). In any case biomass parameters are preserved the same in different bioreactors with different cultivation methods immediately after the transfer (from 0.1 to 3600 seconds) and before the experiment (fluctuation of the parameters not by more than 20%)).

In the preferred embodiment of current invention, method for cloning of the physiological state of microorganisms, continuous cultivation (chemostat, accelerostat, dilutionstat, turbidostat, Z-auxostat, Z-auxoaccelerostat, or a combination of these) is used in the mother reactor. In alternative embodiment batch or fed-batch cultivation is applied. In preferred embodiment the cultivation method applied in the mother reactor is applied also in the daughter reactor. If cultivation method applied in the daughter reactor differs from that in the mother reactor the cultivation parameters are applied in such way, that biomass parameters remain the same as they were in the mother reactor prior to culture transfer within a timeframe of 0.01-3600 seconds (dispersion of biomass parameters not by more than 20% is allowed). In preferred embodiment microorganisms under study are in the steady state but they can be in quasi steady state or in any other state if that state is reproducible by an experimentor with suitable cultivation method.

The reactors in the mother-daughter reactor system are preferentially equipped with sensors, stirrers, inflows (number of inflows is not limited), outflows (number of outflows is not limited), transfer lines connecting the reactors, scales to monitor bioreactor and feed weight (optionally outflow and titrant can be weighted). In an alternative embodiment the material flow is determined by other means, such as mass flow controllers, pump flow rate, weighting the outflow(s), or predicted by modelling.

Depending on the cultivation method and hardware used different pumps, analyzers (e.g. gas analysis, spectrophotometric analysis, chromatography solutions, mass spectrometry solutions, nuclear magnetic resonance or other instrumental analysis solutions), biomass collectors and/or other accessory equipment can be used.

In the present invention following bioreactors can be used: laboratory scale stirred tank reactors, non-laboratory scale stirred tank reactors, plug flow reactors (PFR), airlift reactors, cultivation bag reactors, mini-reactor, micro-reactor, microchip based reactor (lab on a chip) or any other configuration of bioreactor. Mother reactor, which is inoculated by any traditional means, is the reactor from which culture transfer to the other reactors (daughter reactor(s)) takes place. Experiment in the daughter reactor preferentially follows every transfer of biological culture; transfer with the following experiment is regarded as one iteration. Depending on the application used, the mother reactor in one iteration can be a daughter reactor in the next or any other following. The bioreactor system of the current invention is constructed in such manner that biological culture can be transferred from any reactor into any reactor. Reactors in the system can be sterilised and cleaned without detaching the system, cleaning and sterilisation are performed by using sterile chemicals (e.g. water, ethanol). The biological culture transfer lines can be cleaned with sterile gas or other fluidum.

Control of cultivation is performed using software containing control algorithms. In preferred embodiment BioXpert series software and Applikon BioBundle type bioreactors are used, but alternative solutions are suitable. In the preferred embodiment critical control parameters (parameters that depend on reactor volume (dilution rate) or are of important biological nature (gas inflow, dissolved oxygen, T, pH) are controlled with minimal interval at the moment of biological culture transfer (0.01-10 seconds); however, larger interval is suitable if physiological state does not change significantly (more than 20% compared to the initial state in the mother reactor) due to the use of larger interval.

For further clarification of this invention, terms used to describe it are defined as follows:

Accelerostat (A-stat)—cultivation method wherein all cultivation parameters are kept constant apart from dilution rate which is constantly changing according to linear or some other algorithm. If the change of dilution rate is not too fast the microorganisms under study will adapt to the change momentarily; thus each sample in the accelerostat represents a quasi-steady state point in the growth space of the microorganism.

Batch cultivation—feed is inoculated and no substrate is added to the media during fermentation (except substances like oxygen and titrant).

Biomass—portion of biological culture fluid formed by the cells.

Biomass parameters—yields, productivities, doubling time, generation time, (specific) growth rate, biomass concentration, composition and concentration of cell components and metabolites (cell wall components, cell membrane components, periplasm components, cytosol components, DNA, RNA, proteins, mineral substances, metabolites, precursors).

Chemostat—cultivation method operating in continuous manner in steady state. Operates at the substrate limitation conditions.

Continuous cultivation—feed is constantly added into the reactor during fermentation, constant outflow of microorganisms is also present.

Cultivation method—algorithm according to which microorganisms are cultivated. Consists of batch, fed batch and continuous cultivations.

Cultivation parameters—parameters used to control biomass parameters (biomass density, yield, productivity) or altering which is affecting cultivation (for example: dilution rate, pre-given growth rate, temperature setpoint, pH setpoint, pressure setpoint, inflow and outflow of the medium, titration control parameters, aeration control parameters, stirring control parameters, use of different substrates and inhibitors, different concentrations of substrates and inhibitors, length of control interval of different parameters, etc).

Dilution rate—(D) is defined as quotient of the inflow F {L/h} with working volume [L].

Dilution stat (D-stat)—cultivation method where dilution rate is maintained constant while some other environmental parameter is varied in quasi steady state. Essentially, dilution rate indicates how many times the concentration of substances in bioreactor are diluted with inflowing medium within one hour. 1/D provides the time during which substances in bioreactor are diluted two times.

Environmental parameters—environmental parameters that affect the physiology of the microorganisms.

Fed-batch cultivation—cultivation algorithm according to which feed is added to the bioreactor. Fed-batch cultivation is used to control the growth rate, in order to avoid overflow metabolism or technological problems arising from fast growth and high cell density. Usually there is no outflow of effluent fluid.

Fixed physiological state—physiological state is considered to be fixed when the same state is reproducible with applying the same cultivation conditions.

Growth space—N dimensional space which can be described with different physiological states where cells are metabolizing; the axes of this space are environmental and biomass parameters.

Inhibitor—chemical compound or physical entity the application of which has adverse effects to the microorganism's physiology.

Microbial culture—suspension of microorganisms.

Microorganisms—organisms that can be cultivated in bioreactors, for instance bacterial, fungal, mammalian or other cells.

Mother-daughter bioreactor system—technological scheme in which bioreactors are connected with biological culture transfer channels, and in which biological culture transfer from one reactor to another (or several) is possible.

Physiological state of microorganisms—the static and dynamical expression of biomass parameters. Determined by composition, amount and concentration of biomass components, taking into account the possible hysteresis.

PID control—proportional integral derivative control algorithm in regulation theory.

Quasi steady state—a cultivation state wherein biomass parameters are at all times determined by cultivation parameters while some cultivation parameters are altered according to some control algorithm.

Residence time—($\tau$). Defined as 1/D, represents time necessary to dilute substance in bioreactor two times.

Steady physiological state—state of biomass in continuous cultivation where all parameters (environmental and biomass) remain constant in time, in order to achieve steady state at least five residence times of constant environment must be applied.

Steady state—state of biomass in continuous cultivation where all parameters (environmental and biomass) remain constant in time, in order to achieve steady state at least five residence times (5/D) of constant environment must be applied.

Turbidostat—method of continuous cultivation in which biomass concentration is maintained constant by maintaining the optical density constant. Operates at abundance of the substrate.

Variable volume cultivation—cultivation method operating in quasi-steady state in which the only variable parameters are volume of the biological culture and other cultivation parameters controlled by algorithms.

Volume of biological culture—volume of biological culture at given concentration of microorganisms Yield—biomass parameter per consumed substrate unit.

Z-auxoaccelerostat—cultivation method in which biomass concentration is maintained constant by controlling some parameter Z correlating with the concentration of biomass (e.g. pH is decreased as protons are produced); and at the same time an environmental parameter is changed by some pre-given algorithm. Operates at quasi steady state and in abundance of the substrate.

Z-auxostat—method of continuous cultivation where concentration of biomass is preserved constant by controlling some parameter Z, that correlates with the concentration (for example pH) and that can achieve steady state. Operates at steady state and in abundance of the substrate.

BRIEF DESCRIPTION OF THE DRAWINGS

The present invention is explained in more detail with references to the enclosed figures, where.

EXAMPLE

Figure 1:
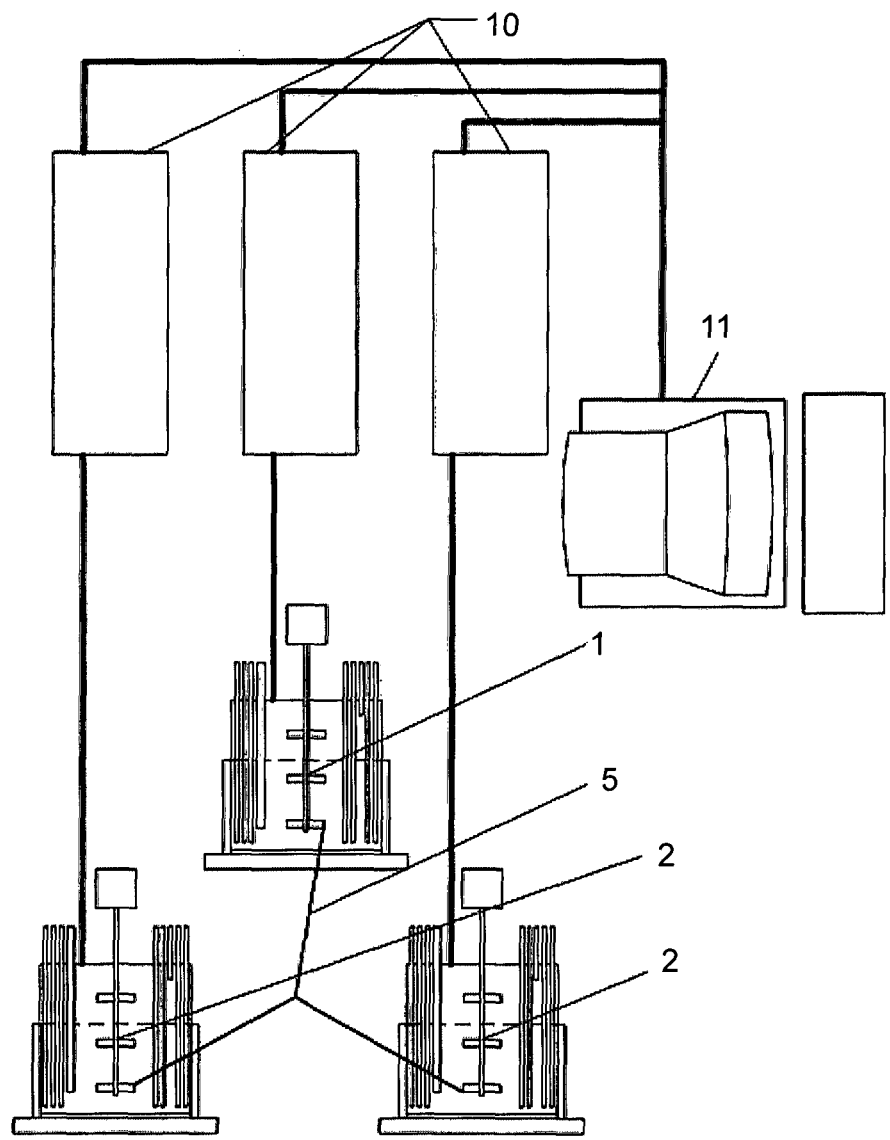
FIG. 1 depicts general scheme of the present invention.
Figure 2:
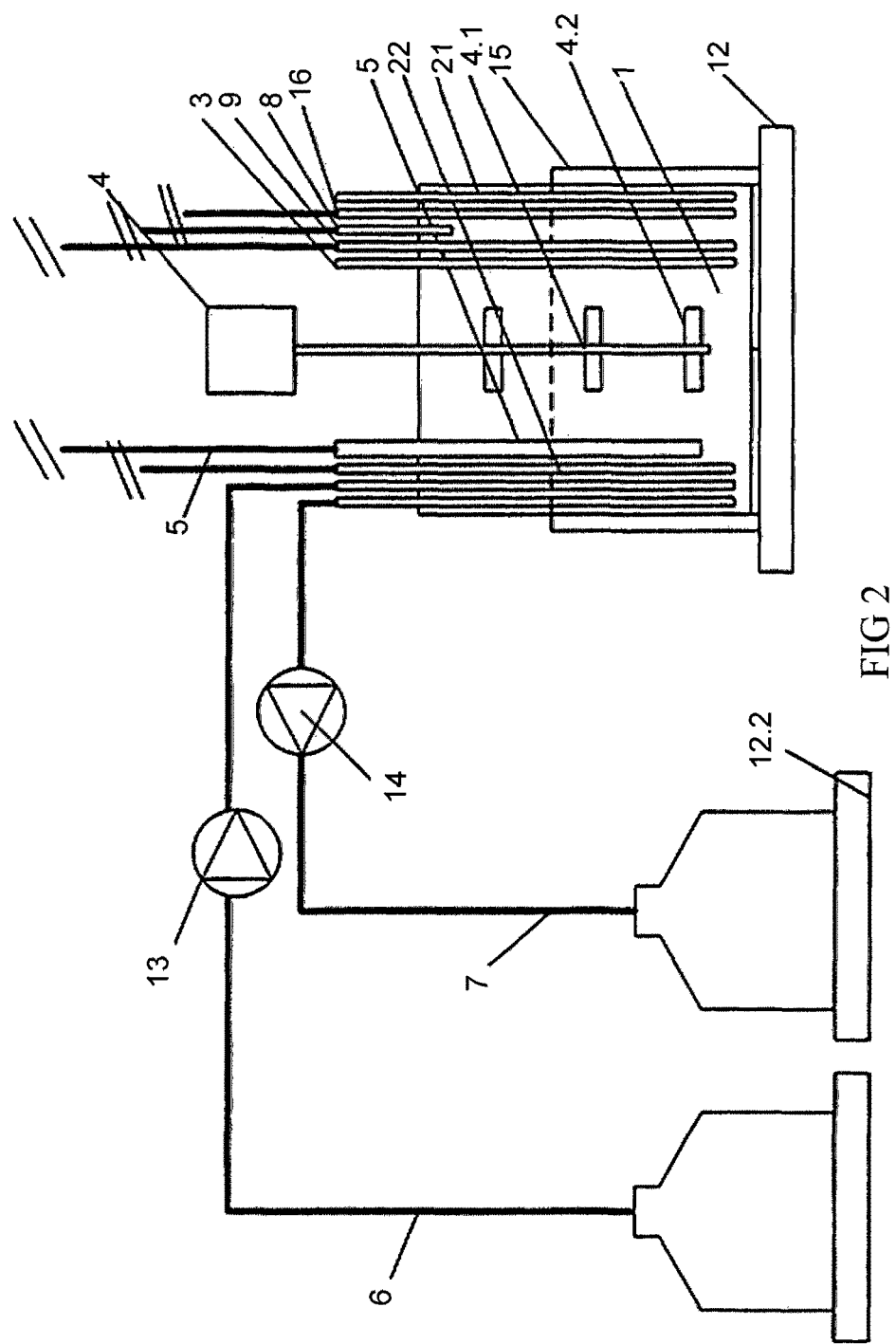
FIG. 2 depicts the transfer units of bioreactor system shown in FIG. 1.
Figure 3:
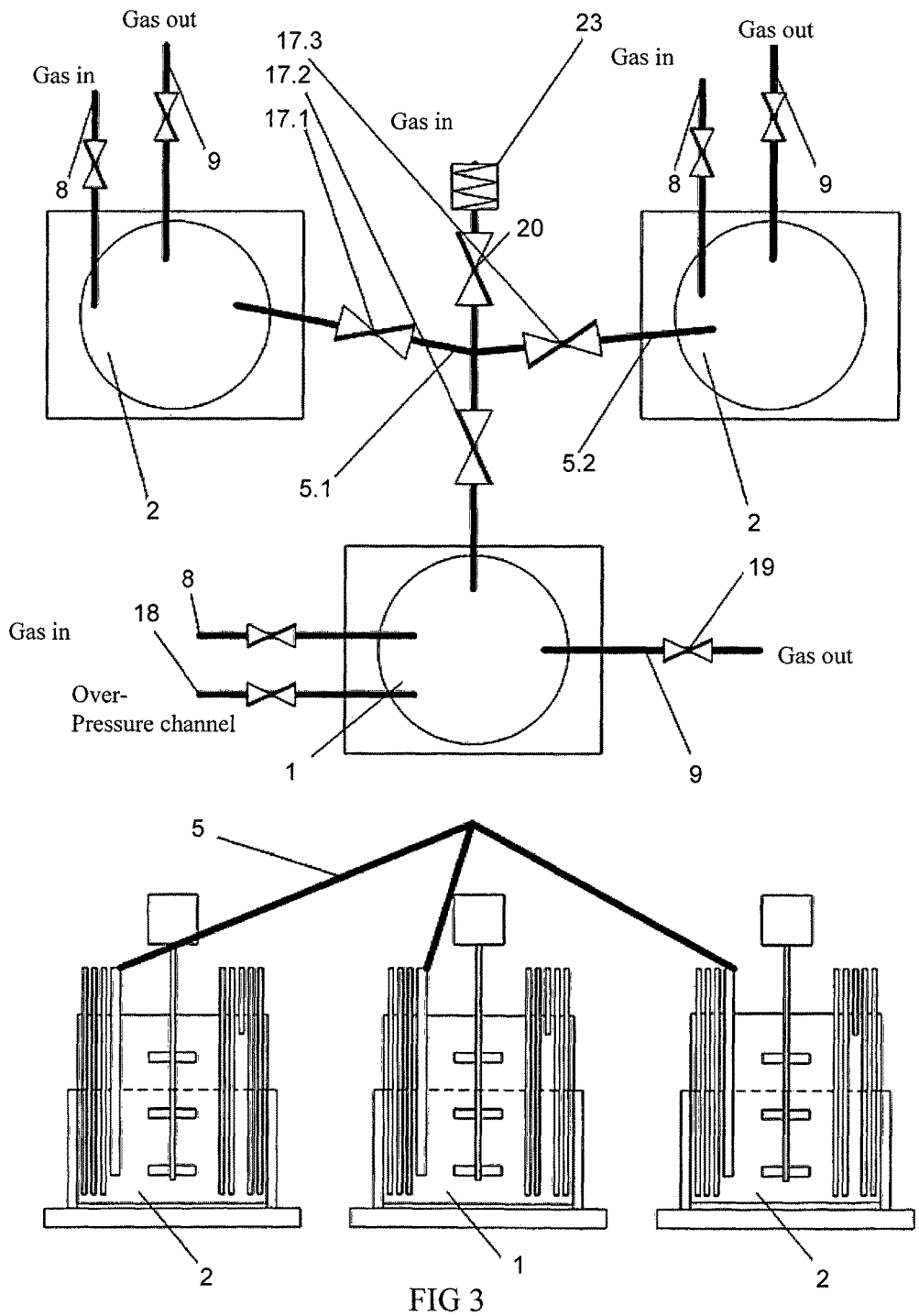
FIG. 3 depicts a detailed overview of the components of bioreactor system shown in FIG. 1.

FIG. 1 depicts the control logic used in the bioreactor system, FIG. 2 depicts bioreactor configuration representing one possible embodiment of the current invention. FIG. 3 depicts bioreactor system with emphasis on the driving force for biological culture transfer—over-pressure. The bioreactor system for multiplying the physiological state of microorganisms comprises of minimally one mother reactor 1 and minimally one daughter reactor 2, mother reactor 1 and daughter reactor 2 are in preferred embodiment equipped with sensors 3, stirrer 4, bioreactor connecting transfer lines 5, fluid inflow 6 and fluid outflow 7, gas inflow 8 and gas outflow 9, controllers 10 connected to the reactors 1 and 2, PC 11 with control software allowing fast enough (0.01-100 seconds) data exchange between control and actuators in critical points of the cultivation (such as culture transfer). Mother reactor 1 and daughter reactor(s) 2 equipped with a device for determining the volume or weight (e.g. scales, sensors, overflow tubes) of the amount of biological culture inside the reactor, the reading of the volume determining device can be stored in PC 11 and used to calculate control values for inflow and outflow pumps 12 and 14. The pumps are controlled such that cultivation parameters during variable volume cultivation, at the moment of biological culture transfer and after that remain constant (deviation in cultivation parameters is tolerated if the resulting fluctuation in physiological state in comparison with the initial physiological state in the mother reactor is less than 20%).

The parameters determined in mother reactor 1 and 2 are sent to cultivation program. Control parameters are sent to all of the controllers 10 in the system. In order to maintain a proper hydrodynamical regime in the reactor during variable volume cultivation the preferred embodiment comprises a stirrer 4 in the mother reactor 1, on the shaft of the stirrer 4.1 there is at least one a turbine mixer 4.2 placed for every diameter of the turbine 4.2. In order to maintain proper dissolved oxygen level in the mother reactor 1 the preferred embodiment has PID control algorithm applied for that purpose.

After variable volume cultivation in the mother reactor 1 the biological culture is transferred to the daughter reactor(s) 2. Daughter reactor(s) 2 are prior to the transfer filled with suitable inert fluid (e.g. physiological solution) and are at the environmental conditions of the mother reactor 1 (deviation of environmental parameters is allowed if the resulting-deviation in physiological state is less than 20%). In order to fill daughter reactor(s) 2 with physiological solution channel 16 is used (driving force can be a pump, over-pressure any other driving force). Briefly before culture transfer the daughter reactor(s) 2 (which are at the same environmental conditions as is the mother reactor 1, (dispersion of environmental parameters is allowed but must not result in alteration of the physiological state of the cells compared to the initial physiological state by more than 20%) are drained via channel 7 (using a pump, over-pressure, under-pressure of any other driving force). Time of drainage is 0.01-36000 seconds. In the preferred embodiment the temperature control of daughter reactor 2 is realized using water jacket 15, any other means are also applicable (such as heating mantle). After the experiment daughter reactor(s) 2 are sterilized in situ via channel 16 with suitable chemical or heat (steam), channel 16 is also used to clean the reactors 2 further with sterilized water.

The channels 5 connecting bioreactors have manually or automatically operated valves 17, and line 5 valves 17.1 and 17.2 (where 0.1 and 0.2 depict number of daughter reactor(s)) can be opened simultaneously, at different times or with pre-given interval in regards to the applying over-pressure to the mother reactor 1. By opening valve 18 extra gas flow to the mother reactor 1 is realized. By closing valve 19 the gas outflow from the mother reactor 1 is closed at the same time or with delay (0.01-36000 seconds) in comparison with the time when the valves 17.1 and/or 17.2 are opened, result of this action is over-pressure in the mother reactor in range of 0.01-100 atm.

To the biological culture transfer line 5.$i$ connecting daughter reactor 2.$i$ with mother reactor 1 is installed a valve 17.$i$ which is opened automatically or manually once biological culture transfer to reactor $i$-1 is finished resulting in biological culture transfer to reactor 2.$i$.

After biological culture transfer the transfer line 5 connecting mother reactor 1 to daughter reactor 2 acts as gas outflow channel, resulting in cleaning of the transfer line 5 from residual biomass. Thus the channel 5.$i$ using which biological culture was transferred last is cleaned.

All transfer channels 5 are cleaned after experiment with sterile gas or fluid input from valve 20.

In order to monitor material flows the volume control devices 12.1 and 12.2 are used, in preferred embodiment these devises are scales by which reactor, feed inflow and outflow are weighted, but alternative methods for determining the volume can be used.

Depending on the cultivation method used the bioreactors can be equipped with accessory devises 21 such as pumps, mass flow controller for monitoring and/or controlling fluid flows, different instrumental analysis hardware (gas analysis, optical density analysis, spectral analysis, chromatography solutions, flow cytometry solutions etc., biomass or supernatant collectors).

In current invention bioreactors are defined as laboratory scale stirred tank reactors, non-laboratory scale stirred tank reactors, plug flow reactors (PFR), airlift reactors, cultivation bag type reactors, mini-reactors, micro-reactors, microchip based reactors (lab on a chip) or any other configuration of bioreactors. Depending on the construction of bioreactor some or all of the hardware mentioned before can be omitted in alternative configurations, with the exception of bioreactors and transfer channels which have to be present.

In preferred embodiment the mother reactor 1 is configured such that cultivation and environmental parameters are fixed unanimously. The cultivation and environmental parameters in daughter reactor(s) 2 are fixed by the operator with control parameters but the number of parameters monitored does not need to be the same as in mother reactor 1. As an example, if the physiological state is monitored using accessory device NMR 21 in the mother reactor 1 then by applying the same cultivation control parameters in the daughter reactor as in the mother reactor it is reasonable to expect the same physiological state to prevail in the daughter reactor(s) 2 as well and there is no need to apply the NMR in the daughter reactor.

In preferred embodiment mother reactor 1 is the bioreactor from which culture transfer is realized and daughter reactor 2 is the bioreactor to which culture transfer is realized. In preferred embodiment the roles of reactors are changeable (in mother reactor of iteration 1 can be daughter reactor in iteration 2).

In the prototype of current invention the reactors comprise of three STR type reactors connected with transfer channel 5. In preferred embodiment the temperature of the reactors is fixed with water jacket type temperature control unit thus fixing temperature with minimal bias from set point value (0.01-5 C) even in the case when no liquid is inside the reactor. In alternative solution other methods for maintaining temperature at set can be used.

The experiment is conducted in daughter reactor(s) 2, variable volume cultivation in the mother reactor 1. Prior to the biological culture transfer process, at the same time when variable volume cultivation is conducted in the mother reactor 1 the environmental parameters in daughter reactor(s) 2 (containing physiological solution) are brought to the same conditions as are in the mother reactor 1 (dispersion of environmental parameters is allowed but must not result in alteration of the physiological state of the cells compared to the initial physiological state by more than 20%).

Once the amount of microorganisms in the mother reactor 1 has reached desired value the daughter reactor(s) are drained within 0.01-36000 seconds using pumps or other means as driving force and biological culture transfer to the daughter reactor(s) is realized. The emptying of bioreactors is conducted such that environmental parameters values in them do not differ from the parameters values prior to the drainage and from those in the mother reactor, and these values will remain the same after culture transfer is finished. The parameter values will remain fixed until experiment is started and the environmental parameter values are changed deliberately. Fluctuation in environmental parameters during drainage and transfer, and after transfer before starting of experiment, less than 20% compared to the parameters value in the mother reactor prior to transfer is allowed, if the effect induced by the fluctuation of environmental parameter does not result in fluctuation in physiological state of the microorganisms more than 20% when compared to the initial state of the microorganisms in the mother reactor, larger deviation of that environmental parameter is allowed.

Prior to biological culture transfer control algorithms and control variables (e.g. pumps) in daughter reactor(s) 2 are turned on, control variables (e.g. pumps) are operated based on cultivation control algorithms. Thus once biological culture transfer into the daughter reactor 2 is started the inflow into these reactors is also started. To achieve matching inflow for the biomass amount transferred the control interval used is in the preferred embodiment a short one, but if longer interval does not interfere with constant physiological state any interval from the range of 0.01-36000 seconds can be applied.

The driving force for the biological culture transfer is in the preferred solution over-pressure, applied to the mother reactor 1 and achieved by initiating extra gassing via valve 18 and turning off the gas outflow from the mother reactor 1 and opening of transfer line 5 simultaneously or with a delay to the first daughter reactor. Once desired volume has been transferred to the first daughter reactor 1 the transfer line to that reactor is closed and transfer line to the next is opened. In alternative solution all the transfer lines 5 to the daughter reactor(s) 2 are opened simultaneously. The transfer line 5 used for the last biological culture transfer is cleaned with gas flowing from the mother reactor 1, the rest of the transfer lines are cleaned after the experiment by applying gas or liquid flow from valve 20.

The system is constructed such that all bioreactors are individually cleanable and sterilised with proper solutions (e.g. sterile deionized water and ethanol) in situ. After sterilization the reactors are rinsed with sterile water to remove any remaining sterilizing agent. Transfer line 5 is in the preferred embodiment inserted into the reactor in such a way that after transfer the remaining biological culture matches the minimal working volume of the reactor, but in alternative solution the transfer line in the reactor can be submerged at whatever necessary depth.

In FIG. 1 the bioreactor system in the preferred solution contains automatically operated valves 17 on the transfer line 5, thus opening/closing of valves 17 is realized automatically. At the same time over-pressure for the transfer is applied in the mother reactor the first biological culture transfer line 5 daughter reactor 2 is opened, after reaching the working volume of that daughter reactor the transfer line to the next daughter reactor 2 is opened. In alternative embodiment the transfer line is opened with delay after applying the overpressure. Process is repeated until last daughter reactor 2 has obtained biological culture in the amount corresponding to its working volume at which moment over-pressure in mother reactor 1 is stopped (valve 18 is closed and valve 19 is opened). During culture transfer the rate of fluid flow is fast enough to avoid substrate consumption during transfer in the transfer line. In the working example with prototype the transfer of working volume of daughter reactor 2 is conducted within 10 seconds.

Figure 4:
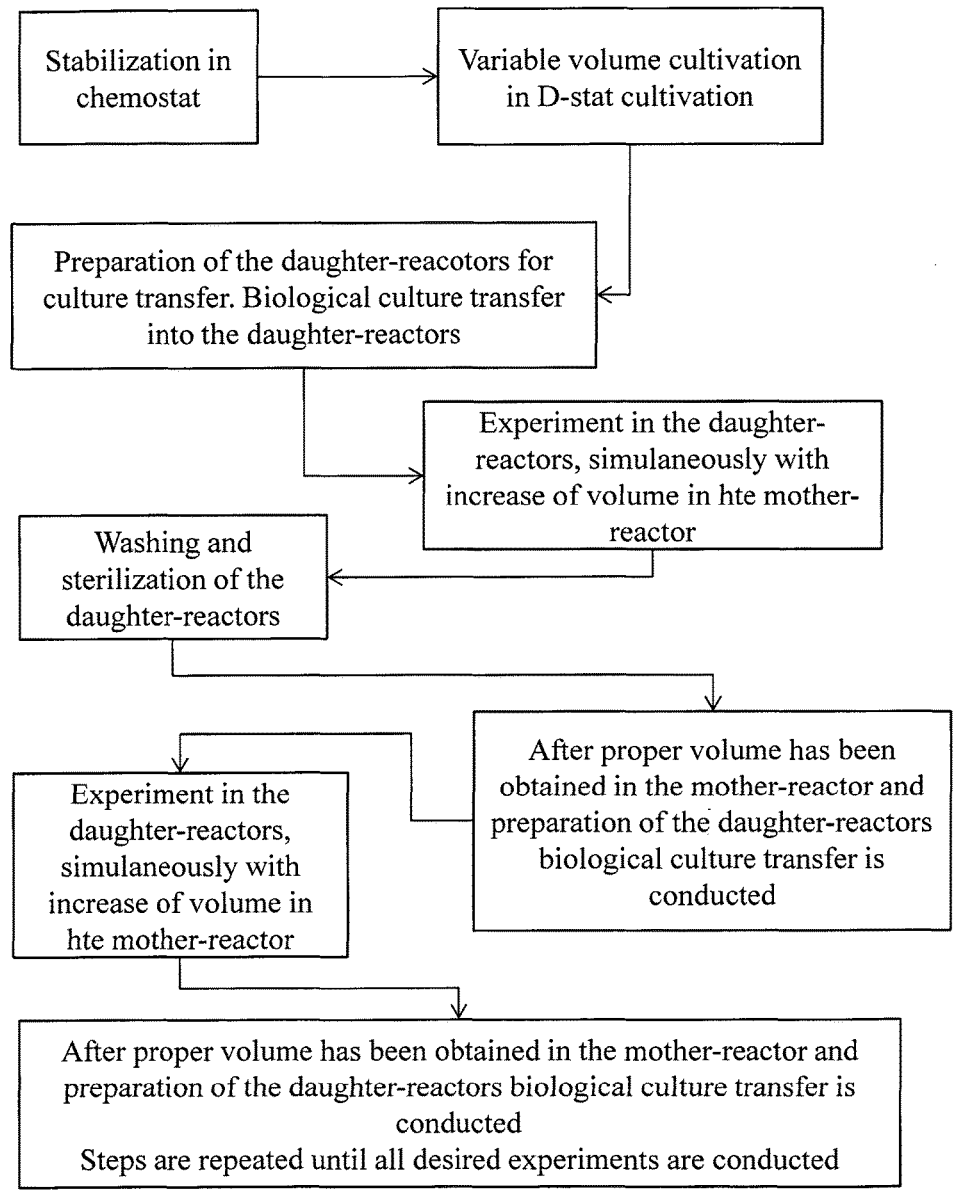
FIG. 4 depicts a block diagram of the method corresponding to the present invention in case of continuous cultivation.

FIG. 4 depicts current invention, method for multiplication of physiological state of microorganisms, flow chart in case of continuous cultivation comprising of the following steps:

Microorganisms stabilisation in chemostat in the mother reactor 1 follows after inoculation and pre-growing the biological culture in periodical cultivation. Stabilisation starts from the moment flow through the reactor is established and lasts for minimum value of five residence times until all cultivation parameters remains constant;

biological culture volume is increased in cultivation using D-stat in mother reactor 1, all other environmental parameters are kept constant and equal to those in the preceding chemostat (dispersion of environmental parameters is allowed but must not result in alteration of the physiological state of the cells compared to the initial physiological state by more than 20%);

at the same time with D-stat cultivation the daughter reactor(s) 2 are prepared for culture transfer and culture transfer is conducted. Culture is transferred to empty preset daughter reactor(s) in which all necessary control algorithm are applied and which environmental parameters match those of the mother reactor prior transfer (dispersion of environmental parameters is allowed but must not result in alteration of the physiological state of the cells compared to the initial physiological state by more than 20%);

experiment is conducted in daughter reactor(s) 2 (the experiment can be continuous cultivation, periodical cultivation, semi-periodical cultivation, or production process), at the same time volume in the mother reactor 1 is increased in D-stat cultivation. The volume increase is preferentially conducted in such a way that guarantees minimum amount of feed spent;

daughter reactor(s) 2 are washed and sterilized;

after setting the daughter reactor(s) 2 to the desired environmental conditions matching those in the mother reactor (dispersion of environmental parameters is allowed but must not result in alteration of the physiological state of the cells compared to the initial physiological state by more than 20%); and after achieving the necessary volume in the mother reactor 1 next culture transfer is conducted;

experiment is conducted in daughter reactor(s) 2 (the experiment can be continuous cultivation, periodical cultivation, semi-periodical cultivation, or production process), at the same time volume in the mother reactor 1 is increased in D-stat cultivation. The volume increase is preferentially conducted in such a way that guarantees minimum amount of feed spent;

daughter reactor(s) 2 are washed and sterilized in situ;

after setting the daughter reactor(s) 2 to the desired environmental conditions matching those in the mother reactor (dispersion of environmental parameters is allowed but must not result in alteration of the physiological state of the cells compared to the initial physiological state by more than 20%) and after achieving the necessary volume in the mother reactor 1 next culture transfer is conducted;

steps are repeated until all desired experiments are conducted.

Figure 5:
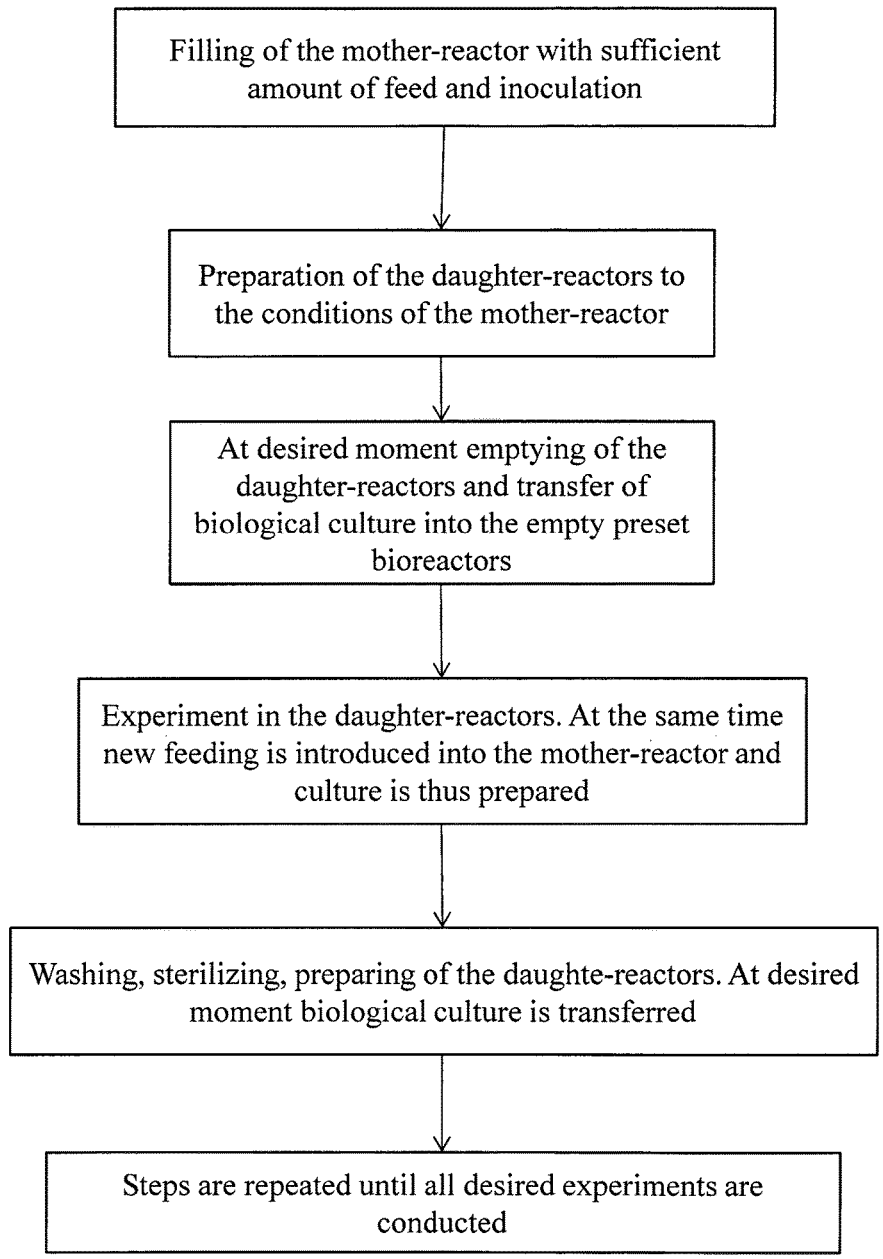
FIG. 5 depicts a block diagram of the method corresponding to the present invention in case of batch cultivation.

FIG. 5 depicts flow diagram of the current invention, method for multiplication for the physiological state of microorganisms in periodical cultivation, comprising of the following steps:

mother reactor 1 is filled with necessary amount of media (the amount should be sufficient enough to fill the working volume of all the daughter reactor(s) 2 in the system) and is inoculated;

daughter reactor(s) 2 are prepared for culture transfer, environmental parameters are set to match those in the mother reactor 1 (dispersion of environmental parameters is allowed but must not result in alteration of the physiological state of the cells compared to the initial physiological state by more than 20%);

upon reaching the desired criteria (biomass density, batch growth phase) the physiological solution in the daughter reactor(s) is discarded and biological culture transfer is conducted. Culture is transferred to empty preset daughter reactor(s) in which all necessary control algorithm are applied and which environmental match those of the mother reactor prior transfer (dispersion of environmental parameters is allowed but must not result in alteration of the physiological state of the cells compared to the initial physiological state by more than 20%);

experiments are run in daughter reactor(s) 2, at the same time necessary amount of biological culture is discarded from the mother reactor 1 and necessary amount of feed is added to the mother reactor 1 (so that biomass density and amount is rendered such that upon experiment end in the daughter reactor(s) 2 and their presetting for next biological culture transfer the biomass in the mother reactor 1 has acquired the necessary characteristics needed to conduct the next experiment in the daughter reactor(s) 2);

daughter reactor(s) 2 are washed and sterilized after conducting the experiment and are prepared for the next biological culture transfer;

upon reaching the desired criteria (biomass density, batch growth phase) the physiological solution in the daughter reactor(s) is discarded and biological culture transfer is conducted. Culture is transferred to empty preset daughter reactor(s) in which all necessary control algorithm are applied and which environmental match those of the mother reactor prior transfer (dispersion of environmental parameters is allowed but must not result in alteration of the physiological state of the cells compared to the initial physiological state by more than 20%);

steps are repeated until all desired experiments have been conducted. The experiment can be continuous cultivations, periodical cultivations, semi-periodical cultivations, or production processes.

Figure 6:
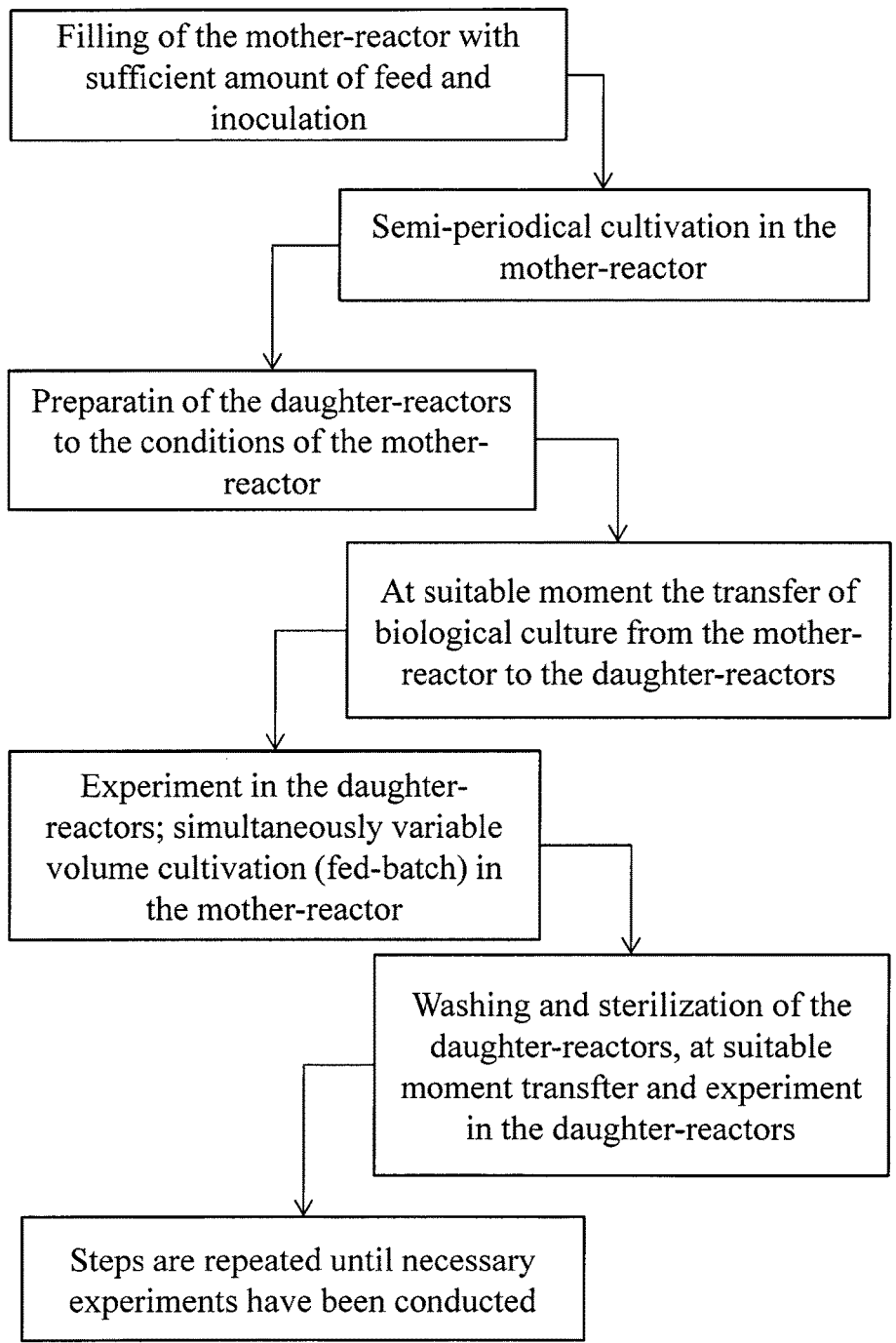
FIG. 6 depicts a block diagram of the method corresponding to the present invention in case of fed batch.

FIG. 6 depicts flow diagram of the current invention, method for multiplication for the physiological state of microorganisms in semi-periodical cultivation, comprising of the following steps:

to the mother reactor 1 feed is introduced and is inoculated with desired microorganisms;

after initial periodical cultivation semi-periodical cultivation is started in the mother reactor 1 to achieve biomass amount necessary for the experiment to be conducted in the daughter reactor(s) 2;

daughter reactor(s) 2 are preset to the conditions of the mother reactor 1 (dispersion of environmental parameters is allowed but must not result in alteration of the physiological state of the cells compared to the initial physiological state by more than 20%);

at desired moment (e.g. at suitable biomass density the biological culture which amount matches the working volume of the daughter reactor 2 is transferred to the daughter reactor 2 while keeping the physiological state of the microorganism the same as it was in the mother reactor 1 prior to the transfer (dispersion of environmental parameters is allowed but must not result in alteration of the physiological state of the cells compared to the initial physiological state by more than 20%);

experiments are conducted in the daughter reactor(s) 2, at the same time biomass in the mother reactor 1 is preset for the next biological culture transfer in terms of volume and concentration by discarding necessary amount of biological culture and by adding necessary amount of feeding media;

daughter reactor(s) 2 are washed and sterilized, and preset for the next biological culture transfer; at the desired moment biological culture transfer is made;

steps are repeated until all desired experiments are conducted, the experiment can be continuous cultivations, periodical cultivations, semi-periodical cultivations, or production processes.

Figure 7:
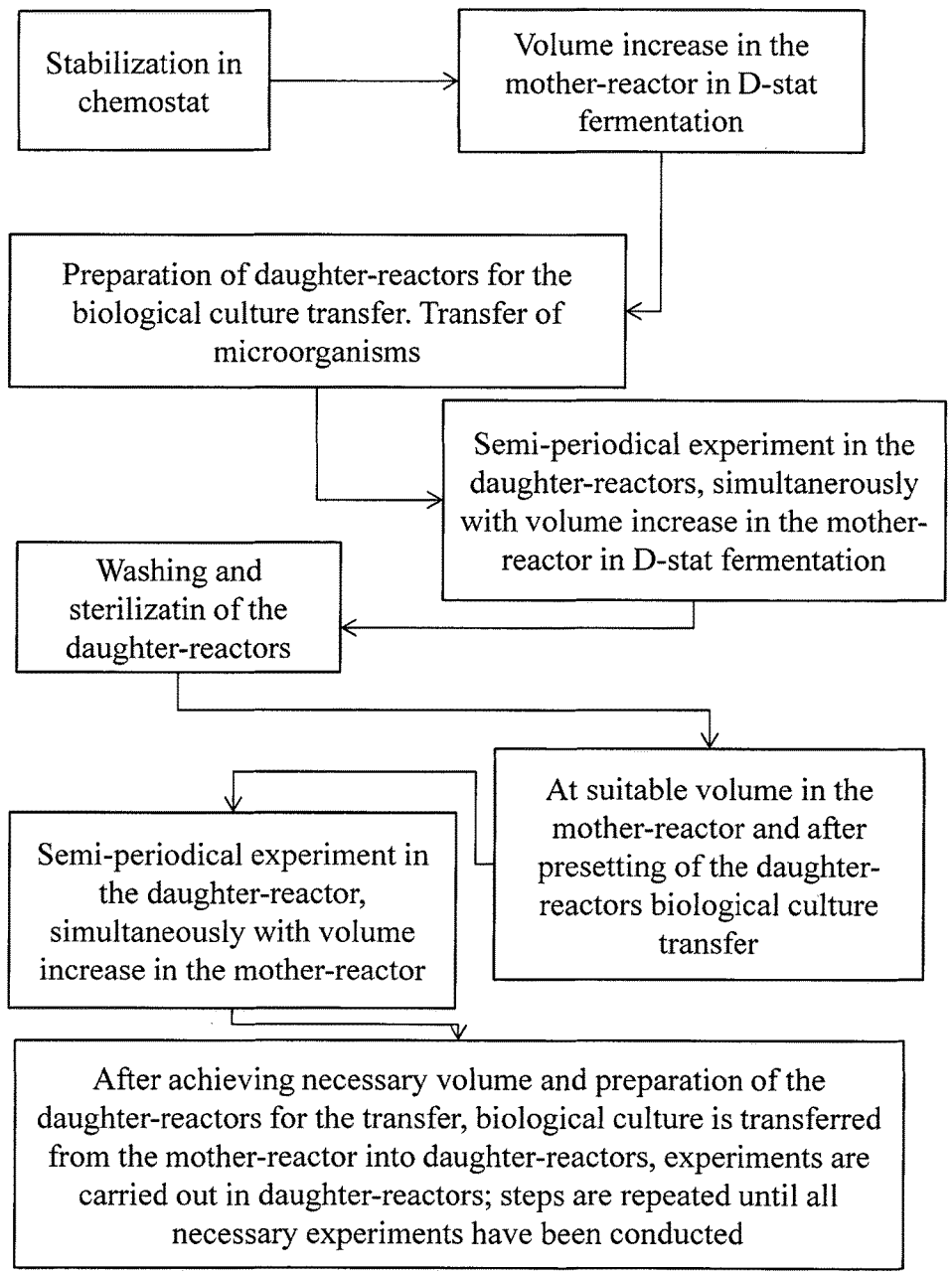
FIG. 7 depicts a block diagram of the method corresponding to the present invention in case different cultivation methods are used in mother- and daughter-reactors.

FIG. 7 depicts flow diagram of the current invention, method for multiplication for the physiological state of microorganisms in continuous cultivation applied in the mother reactor 1 and semi-periodic or periodic cultivation in the daughter reactor(s) 2, comprising of the following steps:

Microorganism's stabilisation in chemostat in the mother reactor 1 follows after inoculation and pre-growing the biological culture in periodical cultivation. Stabilisation starts from the moment flow through the reactor is established and lasts for minimum value of five residence times until all biomass parameters remain constant;

- biological culture volume is increased in cultivation using D-stat in mother reactor 1, all other environmental parameters are kept constant and equal to those in the preceding chemostat (dispersion of environmental parameters is allowed but must not result in alteration of the physiological state of the cells compared to the initial physiological state by more than 20%);
- at the same time with D-stat cultivation in the mother reactor the daughter reactor(s) 2 are prepared for culture transfer and culture transfer is conducted. Culture is transferred to empty preset daughter reactor(s) in which all necessary control algorithm are applied and which environmental parameters match those of the mother reactor prior transfer (dispersion of environmental parameters is allowed but must not result in alteration of the physiological state of the cells compared to the initial physiological state by more than 20%);
- experiment is conducted in daughter reactor(s) 2 (the experiment can be periodical cultivation or semi-periodical cultivation, at the same time volume in the mother reactor 1 is increased in D-stat cultivation. The volume increase is preferentially conducted in such a way that guarantees minimum amount of feed spent;
- daughter reactor(s) 2 are washed and sterilized;
- after setting the daughter reactor(s) 2 to the desired environmental conditions matching those in the mother reactor (dispersion of environmental parameters is allowed but must not result in alteration of the physiological state of the cells compared to the initial physiological state by more than 20%) and after achieving the necessary volume in the mother reactor 1 next culture transfer is conducted;
- experiment is conducted in daughter reactor(s) 2 (the experiment can be periodical cultivation or semi-periodical cultivation), at the same time volume in the mother reactor 1 is increased in D-stat cultivation. The volume increase is preferentially conducted in such a way that guarantees minimum amount of feed spent;
- daughter reactor(s) 2 are washed and sterilized;
- after setting the daughter reactor(s) 2 to the desired environmental conditions matching those in the mother reactor (dispersion of environmental parameters is allowed but must not result in alteration of the physiological state of the cells compared to the initial physiological state by more than 20%) and after achieving the necessary volume in the mother reactor 1 next culture transfer is conducted;
- steps are repeated until all desired experiments are conducted.

Figure 8:
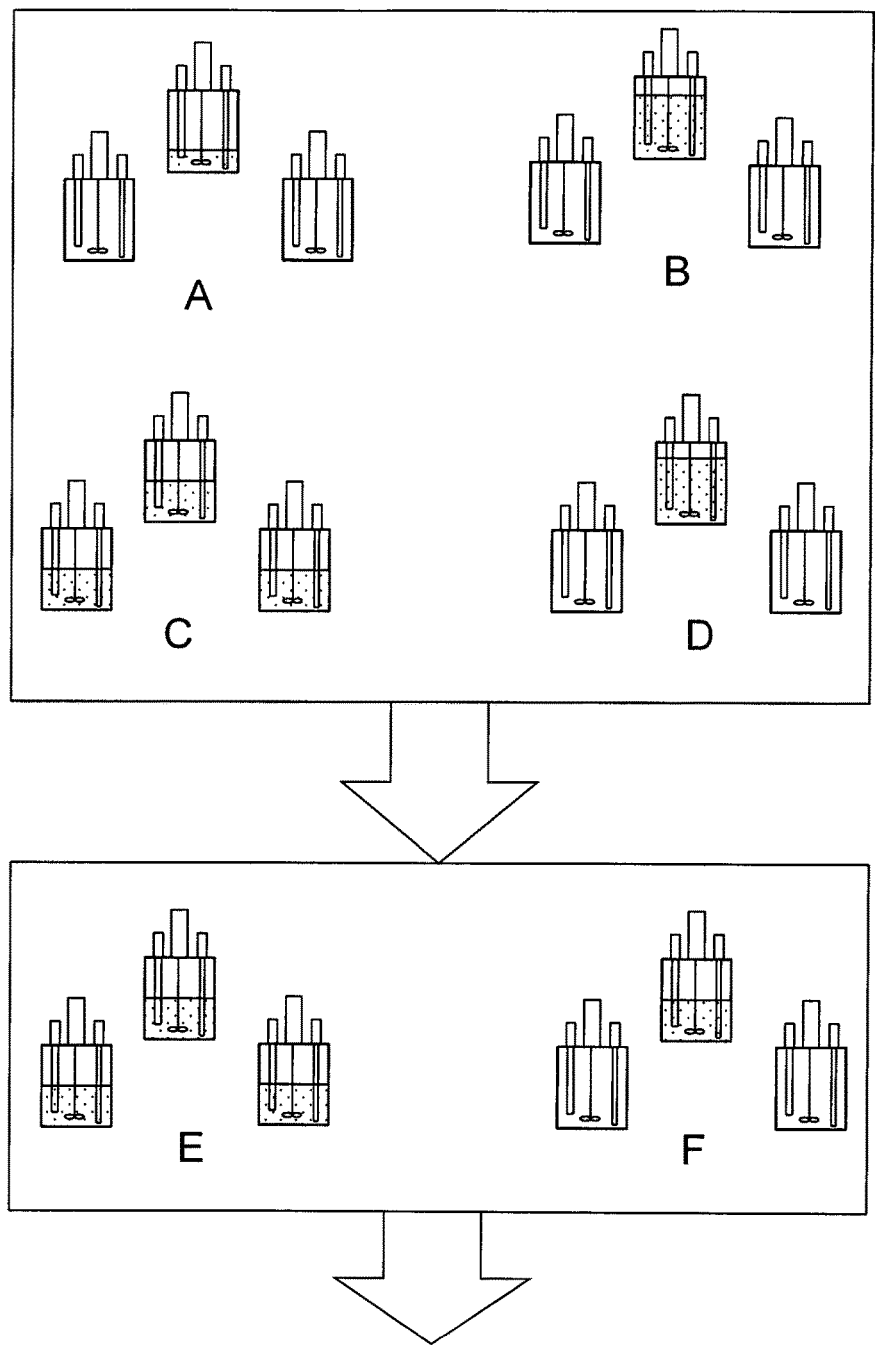
FIG. 8 depicts a cultivation process performed in bioreactor system shown in FIG. 1.

FIG. 8 explains the flow chart depicted in FIG. 4 where cultivation is conducted in a bioreactor system corresponding to current invention in mother reactor 1 and daughter reactors 2.

In the A phase of cultivation the microorganisms are brought to expected density in periodical cultivation and stabilised in chemostat regime. In B the microorganisms are cultivated in variable volume cultivation in D-stat while maintaining the initial physiological state. In alternative solution the physiological state is altered according to preset cultivation algorithms in reproducible manner. In the end of this phase transfer to the daughter reactors 2 ensues. In phase C experiments are conducted in daughter reactors while in the mother reactor 1 variable volume cultivation is conducted in order to obtain proper amount of biomass for the next culture transfer. Preferentially the variable volume cultivation is started at such time that minimal amount of feeding media and cultivation time is spent in the process (variable volume cultivation is started at such time that the necessary amount of culture is obtained at the moment daughter reactors are ready for the next transfer). In phase D daughter reactors 2 are cleaned and sterilized in situ. In that phase, after sterilization and presetting the daughter reactors 2 to the experiment conditions matching those of the mother reactor 1 the next culture transfer is conducted. In phase E the C phase is repeated, in phase F the D phase is repeated. E and F phases are repeated until desired experiments have been conducted.

Figure 9:
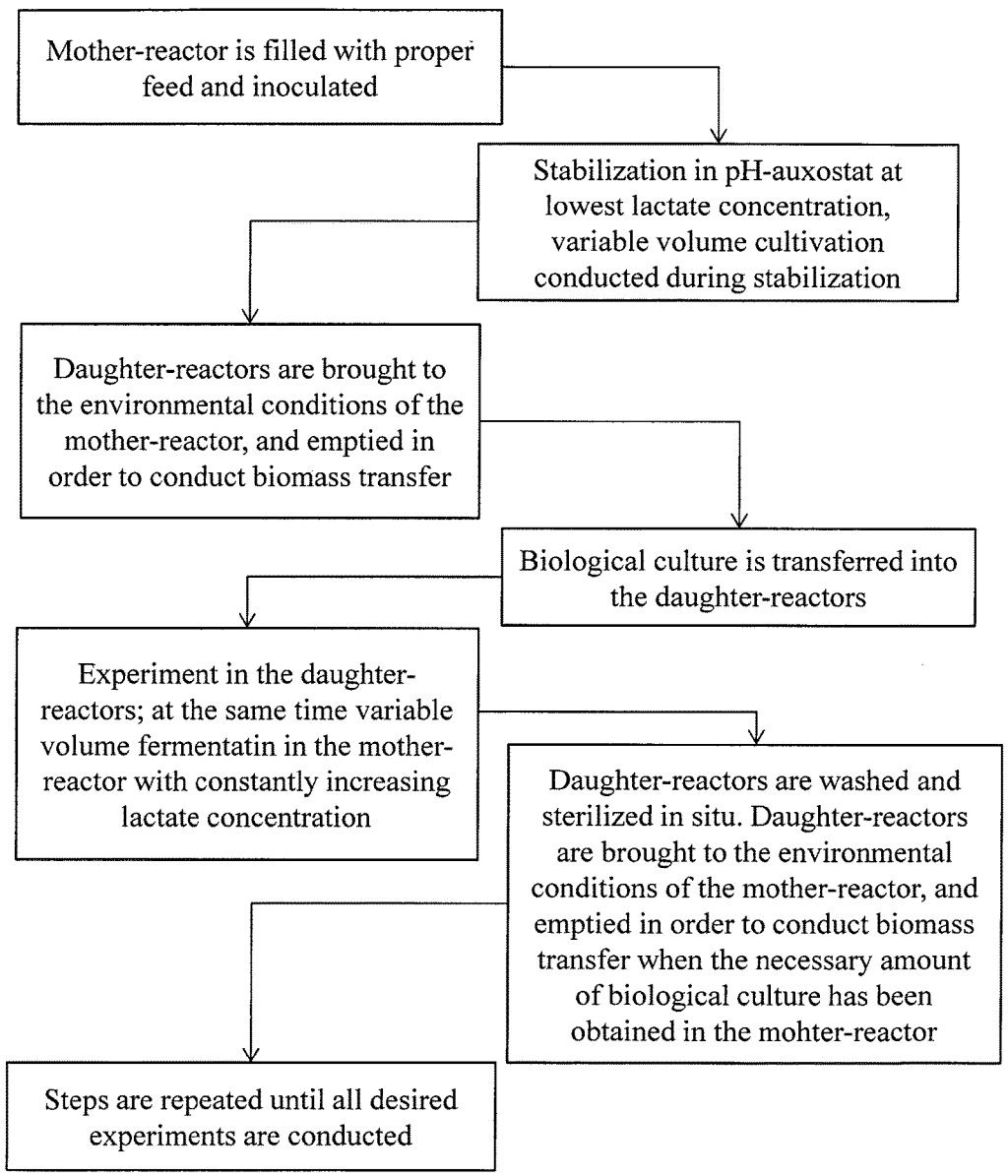
FIG. 9 depicts a block diagram of the method corresponding to the present invention in case of continuous cultivation where the physiological state of the microorganisms is altered according to pre-given algorithm during variable volume cultivation.

FIG. 9 depicts flow diagram of the current invention, method for multiplication for the physiological state of microorganisms in continuous cultivation where the physiological state of the microorganisms is altered during variable volume cultivation in a controlled and reproducible manner; which results in minimal total experiment time. In the example the change in physiology is induced by applying continuous lactate concentration increase in pH-auxoaccelerostat during part of variable volume cultivation such that at the moment of culture transfer the desired lactate concentration has been achieved in the mother reactor. The cultivation is not limited to changing chemicals concentrations; the change of whatever other environmental parameters is applicable. As an example of the experiment in the daughter reactor(s), dissolved oxygen concentration change at fixed lactate concentration set-point can be considered; however any other environmental parameters effect can be elucidated in the experiment.

- Microorganism's stabilisation in pH-auxostat at lowest lactate concentration in the mother reactor 1 follows after inoculation and pre-growing the biological culture in periodical cultivation. Stabilisation starts from the moment flow through the reactor is established and lasts for minimum value of five residence times until all biomass parameters remain constant (the dispersion below 20% is acceptable but in preferred solution not recommended); during stabilisation variable volume fermentation is carried in the mother reactor.
- daughter reactor(s) are brought to the environmental conditions of the mother reactor, and emptied in order to conduct biomass transfer (dispersion of environmental parameters is allowed but must not result in alteration of the physiological state of the cells compared to the initial physiological state by more than 20%);
- biological culture is transferred into the daughter reactor(s) (dispersion of environmental parameters is allowed but must not result in alteration of the physiological state of the cells compared to the initial physiological state by more than 20%);
- experiment in the daughter reactor(s); at the same time variable volume fermentation in the mother reactor with constantly increasing lactate concentration in the end phase of variable volume cultivation (lactate concentration increase is in preferred embodiment conducted such that minimal lactate is spent);
- daughter reactor(s) are washed and sterilized in situ. Daughter reactor(s) are brought to the environmental conditions of the mother reactor (dispersion of environmental parameters is allowed but must not result in alteration of the physiological state of the cells compared to the initial physiological state by more than 20%), and emptied in order to conduct biomass transfer, at suitable moment biological culture is transferred into the preset daughter reactor(s), experiments are carried out in them, simultaneously volume is increased in the mother reactor with constantly increasing lactate concentration in the end phase of variable volume cultivation (lactate concentration increase is in preferred embodiment conducted such that minimal lactate is spent);

steps are repeated until all desired lactate concentrations have been covered.

In the current invention experiment is defined as cultivation experiment (continuous cultivation, semi-periodical cultivation, periodical cultivation or production process using whatever cultivation method (e.g. production of recombinant protein). Immediately after the biological culture transfer and before experiment (0.1 seconds to 1 hour) and if necessary even longer (1 h to 100 h) the physiological state in the daughter reactor(s) 2 is kept the same as it was in the mother reactor 1 prior to the experiment (deviation less than 20% is allowed).

During variable volume cultivation in the mother reactor homogeneous conditions are granted by using proper control algorithms to keep dissolved oxygen and other environmental parameters at set point value. For maintaining hydrodynamic properties equal in the course of the experiment extra turbines are added to the stirrer's shaft. If the physiological state of microorganisms is changed during variable volume fermentation it is conducted reproducibly by applying proper cultivation algorithm (the physiological state's change less than 20% is allowed).

In the current invention, method for multiplying the physiological state of microorganisms the microbes are cultivated in the mother reactor 1 with increasing volume cultivation until volume is reached that is equal to the working volume of all reactors in the system.

Environmental conditions in the daughter reactor(s) 2 brought to the conditions of the mother reactor 1. Microorganisms are transferred from the mother reactor 1 to the daughter reactor(s) 2 and the transfer lines 5 are cleaned from residual biomass.

Multiplication of the physiological state is achieved in the preferred embodiment of the invention by stabilizing biomass in the mother reactor 1 in continuous cultivation (chemostat, turbidostat, accelerostat, auxostat, auxoaccelerostat or a combination of these), after stabilisation the biological culture volume is increased in constant physiology in variable volume cultivation (deviation of the physiology less than 20% is allowed), after reaching the necessary volume biological culture is transferred from the mother reactor 1 to the daughter reactor(s) 2 while maintaining the stabilised physiological state established in the mother reactor before transfer (dispersion of physiological state less than 20% is allowed).

In the daughter reactor(s) 2 experiment or production process is undertaken, after which the daughter reactor(s) 2 are sterilized in situ. Experiment is started from the environmental conditions of the mother reactor 1 (dispersion of environmental parameters is allowed but must not result in alteration of the physiological state of the cells compared to the initial physiological state by more than 20%) and is followed by altering of the environmental parameter of interest at desired time since the biological culture transfer.

Simultaneously with the experiment or production process in daughter reactor(s) 2 the volume in mother reactor 1 is increased to a value that guarantees the volume corresponding to the working volume of all bioreactors in the system into which culture transfer will be conducted.

After experiment or production process the daughter reactor(s) 2 are washed and sterilized in situ. After the experiments the roles of bioreactors can be changed, and the variable volume cultivation can take place in one of the daughter reactor(s) 2 of the previous experiment.

The cultivation method applied in the daughter reactor can be continuous, semi-periodical, or periodical. If the experiment length in the daughter reactor 2 is known it is reasonable to begin with next increase of culture volume in the mother reactor 1 at the time experiment is run in daughter reactor 2, and to reach the desired volume necessary for biological culture transfer at the same time when daughter reactor(s) 2 are ready for the next experiment. If semi-periodical cultivation is applied in the daughter reactor(s) the initial physiological state which prevailed in the mother reactor prior culture transfer (deviation less than 20% is allowed) is applied but the cultivation method is changed (specific growth rate is kept constant, dilution rate is not).

After the effect of desired environmental parameter has been studied or production process conducted the daughter reactor(s) 2 are cleaned and sterilized in situ, preset to the conditions of the mother reactor 1 and another biological culture transfer with the following experiment/production process is undertaken. The process 'experiment-sterilization-transfer' is repeated until all desired experiments or production processes have been conducted.

In order to use continuous cultivation the microorganisms need to be stabilised which takes at least five residence times. Due to that studying of the effect of three inhibitors at ten different concentrations in known solution in three bioreactors at dilution rate 0.2 $h^{-1}$ would take 430 hours. Using the present invention at the same conditions it will only take 139 hours to conduct the same experiment. More details of this example are depicted in Tables 1 and 2. Table 1 depicts the experiment in three bioreactors using traditional approach. Similarly other cultivation experiments or production processes can be run using the system and method described herein.

TABLE 1

Studying of the effect of three inhibitors at ten different concentrations at chemostatic cultivation.

| Activity | Dilution rate | Duration (h) |
|---|---|---|
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 1, 2, 3) | 0.2 | 5.00 |
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 4, 5, 6) | 0.2 | 5.00 |
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 7, 8, 9) | 0.2 | 5.00 |
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 10, 11, 12) | 0.2 | 5.00 |

TABLE 1-continued

Studying of the effect of three inhibitors at ten different
concentrations at chemostatic cultivation.

| Activity | Dilution rate | Duration (h) |
|---|---|---|
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 13, 14, 15) | 0.2 | 5.00 |
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 16, 17, 18) | 0.2 | 5.00 |
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 19, 20, 21) | 0.2 | 5.00 |
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 22, 23, 24) | 0.2 | 5.00 |
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 25, 26, 27) | 0.2 | 5.00 |
| Preparation of bioreactor for the experiment | 0 | 3.00 |
| Pre-growth of microorganisms | 0 | 10.00 |
| Stabilisation at dilution rate | 0.2 | 25.00 |
| Experiment at dilution rate (concentrations of inhibitors 28, 29, 30) | 0.2 | 5.00 |
| Total | | 430 |

TABLE 1

Study of the effect of three inhibitors at ten different concentrations
in three bioreactors using a bioreactor system and a method for
cloning physiological state of microorganisms according to the present
invention at dilution rate 0.2 h$^{-1}$. Increase of the volume
for the following transfers start at the beginning of the experiment
which under current conditions takes 1 h longer than duration
of this experiment. During this time daughter reactor(s) are
prepared (cleaned, sterilised).

| Activity | Dilution rate | Duration (h) |
|---|---|---|
| Preparation of bioreactor for the experiment | 0 | 3.00 |
| Pre-growth of microorganisms | 0 | 10.00 |
| Stabilisation at dilution rate | 0.2 | 25.00 |
| Increasing the volume | 0.2 | 6.00 |
| Experiment; Concentrations of inhibitors 1, 2 | 0.2 | 5 |
| Preparatory phase | 0.2 | 1.00 |
| Experiment; Concentrations of inhibitors 3, 4 | 0.2 | 5 |
| Preparatory phase | 0.2 | 1.00 |
| Experiment; Concentrations of inhibitors 5, 6 | 0.2 | 5 |
| Preparatory phase | 0.2 | 1.00 |
| Experiment; Concentrations of inhibitors 7, 8 | 0.2 | 5 |
| Preparatory phase | 0.2 | 1.00 |
| Experiment; Concentrations of inhibitors 9, 10 | 0.2 | 5 |
| Preparatory phase | 0.2 | 1.00 |
| Experiment; Concentrations of inhibitors 11, 12 | 0.2 | 5 |
| Preparatory phase | 0.2 | 1.00 |
| Experiment; Concentrations of inhibitors 13, 14 | 0.2 | 5 |
| Preparatory phase | 0.2 | 1.00 |
| Experiment; Concentrations of inhibitors 15, 16 | 0.2 | 5 |
| Preparatory phase | 0.2 | 1.00 |
| Experiment; Concentrations of inhibitors 17, 18 | 0.2 | 5 |
| Preparatory phase | 0.2 | 1.00 |
| Experiment; Concentrations of inhibitors 19, 20 | 0.2 | 5 |
| Preparatory phase | 0.2 | 1.00 |

TABLE 1-continued

Study of the effect of three inhibitors at ten different concentrations
in three bioreactors using a bioreactor system and a method for
cloning physiological state of microorganisms according to the present
invention at dilution rate 0.2 h$^{-1}$. Increase of the volume
for the following transfers start at the beginning of the experiment
which under current conditions takes 1 h longer than duration
of this experiment. During this time daughter reactor(s) are
prepared (cleaned, sterilised).

| Activity | Dilution rate | Duration (h) |
|---|---|---|
| Experiment; Concentrations of inhibitors 21, 22 | 0.2 | 5 |
| Preparatory phase | 0.2 | 1.00 |
| Experiment; Concentrations of inhibitors 23, 24 | 0.2 | 5 |
| Preparatory phase | 0.2 | 1.00 |
| Experiment; Concentrations of inhibitors 25, 26 | 0.2 | 5 |
| Preparatory phase | 0.2 | 1.00 |
| Experiment; (Concentrations of inhibitors 27, 28) | 0.2 | 5 |
| Preparatory phase | 0.2 | 1.00 |
| Experiment; Concentrations of inhibitors 29, 30 | 0.2 | 5 |
| Total | | 139.00 |

In the preferred embodiment of the method continuous cultivation is use in mother reactor 1 and daughter reactor(s) 2 and in alternative embodiments periodical of semi-periodical cultivation is used. In the preferred embodiment the microorganisms in the mother reactor 1 are fixed in steady state, in quasi-steady state or in non-steady state; however the microorganisms must be in physiological state determined by and reproducible with the cultivation method applied, and this physiological state be reproducible in the daughter reactor(s) 2 after the biological culture transfer (deviation in the physiological state below 20% is allowed). In the preferred embodiment culture is stabilised in continuous cultivation at minimal working volume in mother reactor 1. This is followed by increasing the amount of microbes at constant concentration in variable volume cultivation in quasi-steady state, meaning that all biomass parameters are kept fixed apart from biological culture volume (dispersion of physiological state below 20% is allowed). The volume in the mother reactor 1 is increased to the level when total working volume of the bioreactors to which the transfer is made into is obtained.

In alternative solution, the physiological state of the microorganisms is changed deliberately during variable volume cultivation; in that case the change in physiology is an anticipated outcome and is well controlled in reproducible manner with the cultivation algorithm applied. In the preferred embodiment, after obtaining the proper biological culture volume the working volume of daughter reactor(s) is transferred into them by means of over-pressure, but under-pressure, pumps or other means can be used. The physiological state of the microorganisms in the daughter reactor(s) 2 should not change due to the transfer of biological culture more than 20% when compared to the physiological state in the mother reactor 1 prior to biological culture transfer.

When aerobic microorganisms are cultivated the dissolved oxygen level is a critical control parameter. The liquid level increase in the bioreactor relative to the turbines on the stirring axis can result in hydrodynamic regime changes affecting solubility of dissolved oxygen. In order to maintain dissolved oxygen at set-point value using PID or other control algorithms for stirring of oxygen addition are applied. Hydrodynamic homogeneity is accomplished by using several turbines on the stirrer shaft, stirring rate can also be modified when needed based on PID or other control regulation.

The present invention, bioreactor system and method for cloning the physiological state of microorganisms is most effective when the number of variable volume cultivations and biological culture transfers are maximal, as stabilisation of the biomass is conducted just once when applying the procedure. In this case the stabilisation phase and preparation time of the reactors is decreased compared to the experiment time is shortened.

The invention claimed is:

1. A method for cloning physiological state of microorganisms utilizing a bioreactor network, and a computer with control software, wherein the bioreactor network includes at least one mother reactor and at least one daughter reactor with roles of the reactors being interchangeable, the method comprising the steps of:
   a) filling the at least one mother reactor with a medium;
   b) inoculating the medium with the microorganisms to obtain a biological culture and optionally stabilizing the biological culture;
   c) applying a cultivation algorithm from the computer with control software;
   d) conducting a variable volume cultivation in the at least one mother reactor, while keeping deviation of biomass parameters within the at least one mother reactor less than 20% or while altering physiological state of the microorganisms within the at least one mother reactor in a controlled and reproducible manner with the cultivation algorithm;
   e) setting up environmental parameters in the at least one daughter reactor in accordance to conditions in the at least one mother reactor;
   f) transferring culture obtained in step d) from the at least one mother reactor to the at least one daughter reactor through at least one transfer channel while keeping deviation of biomass parameters between the at least one mother reactor before the transfer and the at least one daughter reactor after the transfer less than 20% and the transfer is conducted within 0.01-3600 seconds;
   g) cleaning the at least one transfer channel to remove any residual biomass from step f;
   h) conducting a desired experiment to produce desired biomass or metabolites or biological compounds in the at least one daughter reactor;
   i) increasing culture volume in the at least one mother reactor simultaneously to the experiment being conducted in step h);
   j) washing, sterilizing and setting up the at least one daughter reactor for another culture transfer; and
   k) repeating steps f) to j) until all the desired experiments have been conducted.

2. The method according to claim 1, wherein during the transfer of the culture in step f) control interval of 0.01-3600 seconds is applied.

3. The method according to claim 1, wherein the bioreactor network includes at least one mother reactor and at least two daughter reactors and culture transfer from the at least one mother reactor to one daughter reactor is stopped at obtaining working volume of the one daughter reactor at which point a transfer channel between the at least one mother reactor and the one daughter reactor is closed by closing a valve in the transfer channel between the at least one mother reactor and the one daughter reactor and a transfer channel between the at least one mother reactor and an another daughter reactor is opened by opening a valve in the transfer channel between the mother reactor and the another daughter reactor.

4. The method according to claim 1, wherein the cleaning, in step g) is performed by means of a sterile gas from the at least one mother reactor.

5. The method according to claim 1, wherein the increase of culture volume in the at least one mother reactor is accomplished during continuous or fed batch cultivation.

6. The method according to claim 1, wherein a continuous, batch or fed batch cultivation or production process is conducted during the desired experiment in the at least one daughter reactor.

7. The method according to claim 1, wherein the biological compound is selected from the group consisting of DNA, RNA, protein, and polysaccharide.

8. The method according to claim 1, wherein volume in the at least one mother reactor is increased to a value which guarantees a minimal working volume of all reactors in the bioreactor network after the transfer of culture.

9. The method according to claim 1, wherein the bioreactor network includes at least one mother reactor and more than one daughter reactors and the transfer of culture to the daughter reactor(s) is periodical, sequential or in parallel, wherein during the parallel transfer all transfer channels are opened at once and the transfer is preformed to all daughter reactor(s).

10. The method according to claim 1, wherein in the variable volume cultivation an environmental or a cultivation parameter is changed in the at least one mother reactor.

11. The method according to claim 1, wherein driving force for the transfer in step f) is over-pressure or under-pressure.

12. The method according to claim 11, wherein the driving force is over-pressure, and the over-pressure is obtained by closing a gas valve in a gas outflow line of the at least one mother reactor and opening an extra gasssing valve in a gas inflow line of the at least one mother reactor and the over-pressure is stopped by closing the extra gassing valve in the gas inflow line and opening the gas valve in the gas outflow line.

13. The method according to claim 1, wherein during the transfer at step f) to the at least one daughter reactor gas outflow from the at least one mother reactor is closed by a valve at same time as valves of the at least one transfer channel are opened and over pressure of 0.1-100 atm is applied in the at least one mother reactor.

14. The method according to claim 1, wherein the cleaning at step g) is performed by applying a gas or a liquid flow resulting from opening a valve.

15. The method according to claim 1, wherein the variable volume cultivation is performed at a constant concentration of dissolved oxygen, while fluctuation of the concentration is limited to 20%.

16. The method according to claim 15, wherein to improve stirring in the at least one mother reactor, at least one stirrer is applied, wherein the stirrer comprises a shaft and on the shaft at least one turbine mixer placed for every diameter of the turbine.

* * * * *